United States Patent [19]

Gatzke et al.

[11] 4,153,049
[45] May 8, 1979

[54] APPARATUS FOR MAINTAINING SIGNALS WITHIN A GIVEN AMPLITUDE RANGE

[75] Inventors: Ronald D. Gatzke, Lexington; James L. Larsen, Bedford; Elliott S. Simons, Framingham, all of Mass.

[73] Assignee: Hewlett-Packard Company, Palo Alto, Calif.

[21] Appl. No.: 852,170

[22] Filed: Nov. 16, 1977

[51] Int. Cl.² ............................................. D61B 5/04
[52] U.S. Cl. ............................................. 128/419 D
[58] Field of Search ............... 128/2.06 A, 2.06 B, 128/2.06 R, 419 D

[56] References Cited

U.S. PATENT DOCUMENTS

| | | | |
|---|---|---|---|
| 3,442,269 | 5/1969 | Druz | 128/419 D |
| 3,547,108 | 12/1970 | Seiffert | 128/419 D |
| 3,579,138 | 5/1971 | Harris et al. | 128/2.06 B |
| 3,939,824 | 2/1976 | Arneson et al. | 128/2.06 A |

Primary Examiner—William E. Kamm
Attorney, Agent, or Firm—Donald N. Timbie

[57] ABSTRACT

Displayed ECG waveforms are maintained within acceptable aspect ratios without rapid fluctuation in amplitude by rapidly decreasing the gain of the signal channel by discrete amounts as the peak-to-peak amplitude of the ECG signal increases through each of a number of levels and by increasing the gain of the signal channel only after the peak-to-peak amplitude of the ECG signals has dropped to a given fraction for a predetermined period of time.

4 Claims, 3 Drawing Figures

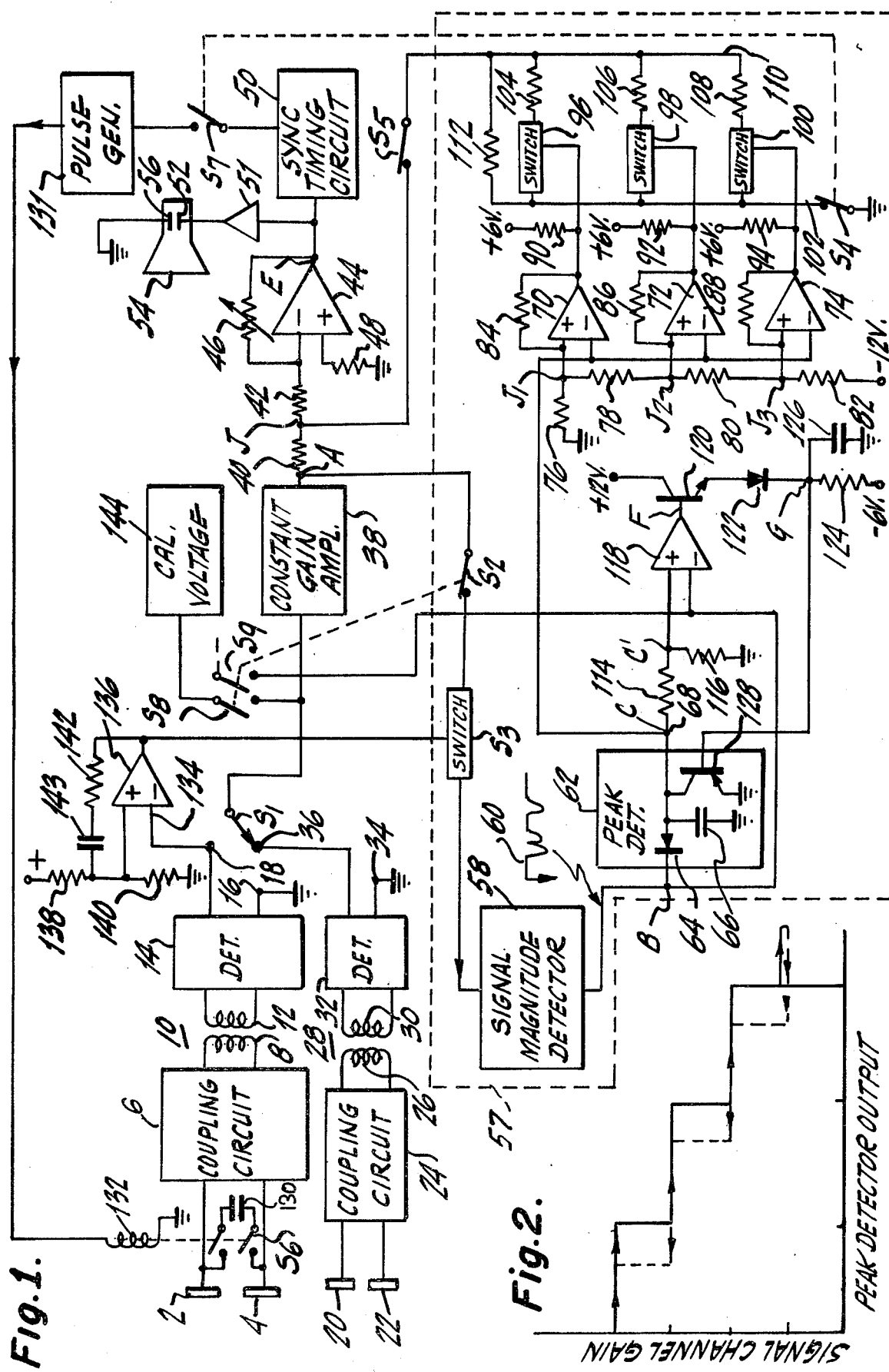

AGC WAVEFORMS

APPARATUS FOR MAINTAINING SIGNALS WITHIN A GIVEN AMPLITUDE RANGE

BACKGROUND OF THE INVENTION

Before a defibrillator is triggered so as to discharge a pulse of current between the paddle electrodes held against a patient's chest, it is necessary to determine the action of the heart. To do this, electrical signals that represent heart action are obtained from the paddle electrodes or from a set of ECG electrodes, amplified in a signal channel, and displayed as a waveform by an oscilloscope or by some other suitable means. If the displayed waveform indicates that the heart is operating in a random fashion, known as fibrillation, the defibrillator can be discharged, but if the display indicates that the heart is operating cyclically, other types of treatment are generally used. The waveform for each heart cycle is generally comprised of a sequence of positive and negative peaks having different amplitudes. Under the conditions prevailing when a defibrillator is in use, the peak-to-peak amplitude and hence the aspect ratio of the different sequences of signals can change rapidly by such large amounts as to make analysis of the displayed waveform difficult or impossible. In order to keep the aspect ratio within limits that medical personnel are used to interpreting, it is generally necessary to adjust the gain of the signal channel. If this is done manually, it can cause significant delay in the vital resuscitation precedure, especially where there is only one operator. Therefore, it is desirable to provide circuits for automatically controlling the gain. Circuits that use negative feedback to continually adjust the gain cause distortion in the waveform of the heart action that may be particularly disadvantageous when the defibrillator is being used to monitor the patient.

BRIEF DISCUSSION OF THE INVENTION

In a preferred embodiment of this invention, an automatic gain control circuit is provided wherein the signals representing heart action are applied to a full wave rectifier so as to make all signal peaks have the same polarity. The output of the rectifier is applied to a peak detector, and its output is applied to switching means for quickly attenuating the signals flowing in the signal channel by predetermined amounts whenever the output of the peak detector exceeds one of several given amplitudes. Means are provided for resetting this peak detector whenever the output of the full wave rectifier falls below a given fraction of the output of the peak detector for a given period of time.

Provision is made for decoupling the automatic gain control circuit whenever a defibrillation pulse occurs, for isolating the circuit whenever calibration pulses are present, and for disabling the automatic gain during synchronous operation when the ECG signals are being used to control the timing of the defibrillation pulse.

THE DRAWINGS

FIG. 1 is a schematic diagram of an automatic gain control circuit of the invention.

FIG. 2 is a graphical illustration of the effect of one hysteresis in the circuit.

Figure 3:
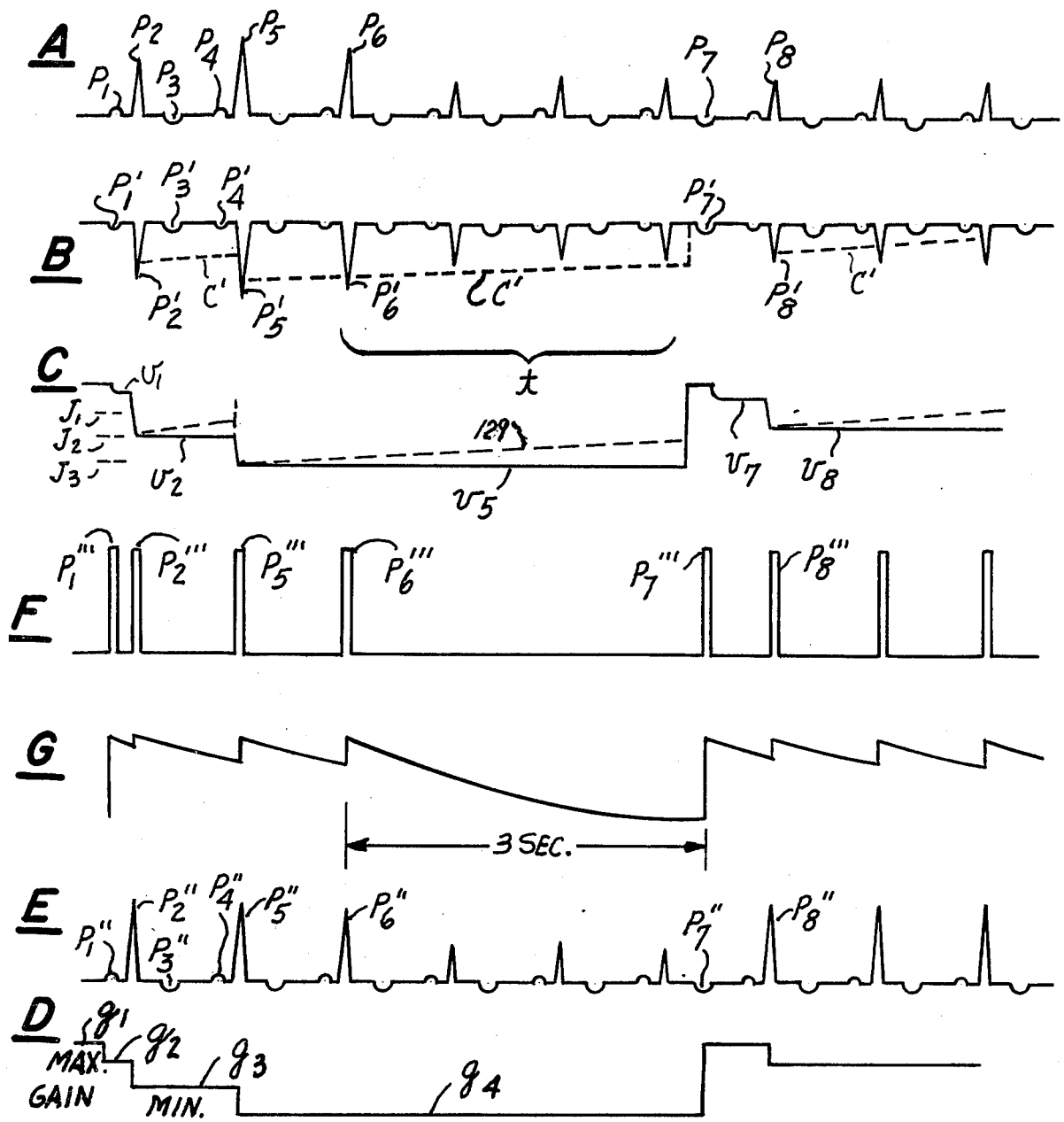
FIG. 3 is a series of graphs used in explaining the operation of the circuit of FIG. 1.

What immediately follows is a description of the standard portions of a defibrillator shown in FIG. 1 that are involved with this invention. Differential signals provided by defibrillator paddles 2 and 4 are coupled by a circuit 6 to the primary winding 8 of a transformer 10 and by the secondary winding 12 to a detector 14 that has a single-ended output comprised of a grounded terminal 16 and an ungrounded terminal 18. In a similar manner, differential signals provided by the ECG electrodes 20 and 22 are coupled by a circuit 24 to the primary winding 26 of a transformer 28 and by its secondary winding 30 to a detector 32 that has a single-ended output comprised of a grounded terminal 34 and an ungrounded terminal 36. The signals at the output terminals 18 and 36 may be positive or negative with respect to ground, depending on the polarity of the differential signals. A switch $S_1$ is provided for selectively connecting the output terminal 18 of the detector 14 or the output terminal 36 of the detector 32 to the input of a constant gain amplifier 38. Its output is connected by series resistors 40 and 42 to the inverting input of an operational amplifier 44, the gain of which may be manually adjusted by a variable resistor 46 connected between its output and its inverting input. The non-inverting input of the amplifier 44 is connected to ground by a resistor 48. The output of the amplifier 44 is connected to the input of a sync timing circuit 50 and via an amplifier 51 to a deflection plate 52 of an oscilloscope 54. The other deflection plate 56 is grounded. Thus, depending on the position of the switch $S_1$, electrical signals representing cardiac action are coupled from the paddle electrodes 2 and 4 or from the ECG electrodes 20 and 22 via the signal channel just described to the inputs of the sync timing circuit 50 and the deflection plate 52 of the oscilloscope 54.

In accordance with this invention, the gain or amplification of the signal channel is controlled by the circuits in the dotted rectangle 57. Basically, it operates by providing different amounts of resistance between the junction J of the resistors 40 and 42 and ground so as to form a potential divider with the resistor 40 that controls the fraction of the signal appearing at the output of the constant gain amplifier 38 that is applied to the amplifier 44.

The full output of the constant gain amplifier 38 is coupled via a normally closed switch $S_2$ and a normally closed solid state switch $S_3$ to a signal magnitude detector 58 which may take the form of a full wave rectifier, a half-wave rectifier, an RMS detector or any means for causing all pulses in the ECG signals to have the same polarity with respect to ground as indicated by the waveform 60. The output of the signal magnitude detector 58 is applied to a peak detector 62. Although the peak detectors may include other components, the essential ones from a functional viewpoint are a diode 64 and a storage capacitor 66 that are effectively coupled in series between the output of the detector 58 and ground. The peak voltage appearing across the storage capacitor 66 is coupled to the output 68 of the peak detector 62. The output 68 is connected to the inverting inputs of comparators 70, 72 and 74. Resistors 76, 78, 80 and 82 are connected in series between ground and a negative voltage such as $-12v$, and their junctions $J_1$, $J_2$ and $J_3$ are connected respectively to the non-inverting inputs of the comparators 70, 72 and 74. Hysteresis resistors 84, 86 and 88 are respectively connected between the outputs of the comparators 70, 72 and 74 and their non-inverting inputs. Equal valued resistors 90, 92 and 94 are respectively connected between the outputs of the comparators 70, 72 and 74 and a point of positive potential such as $+6v$. One side of each of solid state switches 96, 98 and 100 is connected to a bus 102 that is connected via a normally closed switch $S_4$ to ground, and the other sides of the switches are respectively connected via resistors 104, 106 and 108 to a bus 110 that is connected via a normally closed switch $S_5$ to the junction J of the resistors 40 and 42. The outputs of the comparators 70, 72 and 74 are respectively connected to the control inputs of the switches 96, 98 and 100. A resistor 112 is connected between the buses 102 and 110.

The following circuitry operates to permit the gain to be changed after the peak amplitude of the ECG signals has decreased by a given fraction for a selected period of time. The output 68 of the peak detector 62 is connected to ground via a voltage divider comprised of two series resistors 114 and 116. The reduced voltage at their junction is coupled to the non-inverting input of a comparator 118, and the inverting input of the comparator 118 is connected to the output of the signal magnitude detector 58. The output of the comparator 118 is connected to the base of an NPN transistor 120 having its collector connected to a positive voltage, e.g., +12v, and its emitter coupled to a negative voltage, e.g., −6v, via a diode 122 and a resistor 124 connected in series. The junction of the diode 122 and the resistor 124 is connected via a capacitor 126 to ground and also to the base of a PNP transistor 128. The collector of the transistor 128 is connected to the ungrounded side of the storage capacitor 66, and its emitter is connected to ground.

OPERATION

FIG. 3 includes waveforms which might appear at points in the circuit of FIG. 1 designated by the same letters. In all these waveforms, the baseline represents ground. Waveform A shows an ECG signal including peaks $P_1$ through $P_8$ that might appear at the output of the constant gain amplifier 38. This signal is applied via the normally closed switches $S_2$ and $S_3$ to the input of the signal magnitude detector 58. If the detector 58 is a full wave rectifier, its output may be as indicated by waveform B in which all peaks point in a negative direction. The peaks $P_1$ through $P_8$ of the waveform A appear as peaks $P_1'$ through $P_8'$ in the waveform B. Application of the voltage (illustrated by the waveform B) to the peak detector 62 charges the capacitor 66 to voltages (indicated by the waveform C) that are very nearly equal to the highest voltage applied to the peak detector, so that the peaks $P_1'$ and $P_2'$ successively produce the negative voltages $v_1$ and $v_2$ across the capacitor 66. The peaks $P_3'$ and $P_4'$ have no effect as they are smaller than $P_2'$, but the peak $P_5'$, being larger than $P_2'$, charges the capacitor 66 to a greater negative voltage $v_5$. The solid line of waveform C illustrates the situation where the capacitor 66 has no leakage, and the dotted line 129 indicates a situation where it has leakage.

When all of the switches 96, 98 and 100 are open, only the resistor 112 is connected between the junction J of the resistors 40 and 42 and ground. This creates the maximum gain condition, as indicated by $g_1$ in the waveform D. As the voltage C at the output 68 of the peak detector 62 passes through the voltages at the junctions $J_1$, $J_2$ and $J_3$ that are indicated on the waveform C, the outputs of the comparators 70, 72 and 74 become positive so as to successively close the switches 96, 98 and 100. Thus, when the voltage C reaches the voltage at $J_1$, the switch 96 is closed so as to place the resistor 104 in shunt with the resistor 112. This lowers the resistance between the junction J of the resistors 40 and 42 and ground, thereby reducing the fraction of the signal from the constant gain amplifier 38 that is applied to the amplifier 44. This reduces the gain of the signal channel from $g_1$ to $g_2$, as indicated by the waveform D. When the voltage C reaches the voltage at $J_2$, the switch 98 closes so as to place the resistor 106 in parallel with the resistors 112 and 104 and lower the gain of the signal channel from $g_2$ to $g_3$. Similarly, when the voltage C reaches the voltage of the junction $J_3$, the switch 100 is closed, placing the resistor 108 in parallel with the resistors 112, 104 and 106 and reducing the gain to a minimum $g_4$. As a result of these changes in the gain of the signal channel, the peaks $P_1$ through $P_6$ of the waveform A appear as peaks $P_1''$ through $P_6''$ at the output of the amplifier 44, as shown in the waveform E. Note that the peaks $P_2''$, $P_5''$ and $P_6''$ have nearly the same amplitude as is desired.

The purpose of the resistors 84, 86 and 88 is to provide hysteresis so that once the switches 96, 98 or 100 have been closed so as to reduce the gain, they will not be reopened so as to increase the gain by a momentary reduction in the signal provided by the peak detector 62, such as can occur in the presence of noise. The hysteresis also prevents the comparators 70, 72 and 74 from reverting to a low output and reopening the switches in the presence of normal leakage in the capacitor 66, such as indicated by the dotted line 129 in waveform C.

The operation just described applies to a situation where each succeeding ones of the larger peaks such as $P_2$, $P_5$ and $P_6$ is either larger or not much smaller than the one preceding it. If nothing more is done, the gain cannot be made to increase so as to make the smaller peaks that follow the peak $P_6$ of the waveform A have the desired amplitude. In order to do this, the peak detector is reset as follows. The voltage at the output of the detector 58, illustrated by the waveform B, is applied to the inverting input of the comparator 118. As previously stated, the output of the peak detector 62 is applied via resistors 114 and 116 to the non-inverting input of the comparator 118. If the resistance of the resistor 116 is twice the resistance of the resistor 114, the voltage at their junction will be two-thirds of the output voltage of the detector 62, represented by the solid line of the waveform C, providing there is no leakage in the capacitor 66, and two-thirds of the voltage represented by the dotted line 129 if there is leakage. This latter two-thirds voltage is superimposed on the waveform B, as indicated by the dotted line C'. Whenever the peaks of the waveform B are greater than the voltage of C', the comparator 118 outputs positive pulses of equal amplitude. Accordingly, the peaks $P_1'$, $P_2'$, $P_5'$ and $P_6'$ of the waveform B produce peaks $P_1'''$, $P_2'''$, $P_5'''$ and $P_6'''$ at the output of the comparator 118, as indicated by the waveform F. Application of these peaks to the base of the transistor 120 causes it to conduct and charge the capacitor 126, as indicated at the vertical portions of the waveform G. In between peaks, the capacitor 126 discharges, as indicated by the sloping portions of the waveform G. As long as the voltage across the capacitor 126 is positive with respect to ground, it keeps the transistor 128 biased to cut off, but when the peaks at the output of the detector 58 are less than the voltage C', the capacitor 126 is not recharged and continues to discharge. If the capacitor 126 completely discharges, as indicated at the end of the time t, the transistor 128 conducts and discharges the capacitor 66 so as to reset the peak detector 62. The capacitor 66 is then ready to be charged again by the output of the detector 58 so that the peaks P$_7$ and P$_8$ produce the voltages v$_7$ v$_8$ across the capacitor 66, as shown in the waveform C, and cause the comparator 118 to output the peaks P$_7'''$ and P$_8'''$. Because the latter peaks are less than t seconds apart, they keep the capacitor 126 sufficiently charged to cut off the transistor 128.

SPECIAL CONTROLS

Defibrillation pulses are applied to the paddles 2 and 4 by respectively connecting them to opposite sides of a storage capacitor 130 by means of a switch S$_6$ that may be operated manually or automatically. Whether the switch S$_1$ is connected to the output terminal 18 so as to supply ECG signals derived from the paddles 2 and 4 to the input of the constant gain amplifier 38 or to the output terminal 36 so as to supply ECG signals from the ECG electrodes 20 and 22 to the input of the constant gain amplifier 38, the defibrillation pulse causes a pulse of voltage to appear at the input of the constant gain amplifier that is much greater in amplitude than any peak of the ECG signals. If this large voltage pulse is permitted to reach the input of the detector 58, the capacitor 66 of the peak detector 62 would be highly charged so as to reduce the gain of the signal channel to a minimum. No higher gain could be set until the capacitor 66 is discharged, and as this might take considerable time, the ECG signals occurring in the meantime would be distorted. In order to prevent this from occurring, the defibrillation pulse at the output 18 of the detector 14 is applied via a lead 134 to the inverting input of a comparator 136. Its non-inverting input is connected to the junction of resistors 138 and 140 that are connected in series between a point of positive voltage and ground. During the presence of the defibrillation pulse, the voltage at the non-inverting input is less than the voltage at the inverting input, so that the output of the comparator 136 becomes negative and opens the solid state switch S$_3$ for a time determined by a resistor 142 and a capacitor 143 that are connected in series between the output of the comparator 136 and its non-inverting inputs. This interrupts the flow of ECG signals to the input of the full wave rectifier 58 as required.

During synchronous operation, it is desirable that the gain of the signal channel be controlled by the potentiometer 46 rather than the AGC circuit 57. Synchronous operation is attained by closing the switch S$_7$ so as to couple the synchronous timing circuit to a pulse generator 131 and cause it to output a pulse at the proper time during each heart cycle. This pulse is applied to an electromagnetic plunger 132, closing the switch S$_6$ and discharging the storage capacitor 130 through the paddles 2 and 4. Disabling of the AGC circuit is accomplished by ganging the switch S$_7$ with the switch S$_4$ so that when S$_7$ is closed, S$_4$ is opened. The opening of S$_4$ breaks the circuit between the junction J and ground so that the full ECG signal is applied to the amplifier 44.

Calibration of the amplitude of waveforms on the oscilloscope 54 is attained by applying a pulse of calibrated voltage to the input of the constant gain amplifier 38. As shown, this function is performed by momentarily closing a switch S$_8$ and a source 144 of calibration voltage. During the presence of the calibration pulse, it is necessary to prevent the charge on the capacitor 66 of the peak detector 62 from being affected so the system gain will not be changed by the pulse. This is done by ganging a normally open switch S$_9$ and the normally closed switch S$_2$ with the normally open calibration switch S$_8$. When S$_9$ is momentarily closed, it applied a pulse of negative voltage to the inverting input of the comparator 118 so as to keep the storage capacitor 66 in the peak detector 62 from being discharged. The opening of the normally closed switch S$_2$ prevents the calibration pulse from being applied to the full wave rectifier 58.

Whereas this invention has been described in terms of a hardware circuit, it will be understood by those skilled in the art that it could be carried out by use of a computer and suitable programs.

What is claimed is:

1. Apparatus for controlling the amplitude of information signals flowing in a signal channel that may have peaks on either side of a baseline comprising, a signal channel having an input to which the information signals may be applied and an output for passing information signals, a signal magnitude detector having an input to which said information signals may be applied and an output, peak detecting means having a memory and having an input and an output, said input being coupled to said output of said signal magnitude detector, gain control means having an input coupled to the output of said peak detecting means for changing the gain of said signal channel from one discrete value to another as the voltage at the output of said peak detecting means increases through each of a plurality of predetermined levels, and reset means for resetting said peak detector when the voltage at the output of said signal magnitude detector is less than a given fraction of the voltage at the output of said peak detector for a predetermined length of time.

2. Apparatus as described in claim 1 wherein means are provided for applying a calibration pulse to an input of said signal channel, and means are provided for disabling said reset means and interrupting the application of signals to the input of said signal magnitude detector during the application of said calibration pulses to said channel.

3. Apparatus as set forth in claim 1 wherein said gain control means (decreases) includes means for decreasing the gain of said signal channel by given increments as the voltage at the output of said peak detector rises through each of a first group of levels and wherein the gain control means (increases) includes means for increasing the gain of said signal channel by the same increments as the voltage at the output of said peak detector decreases through each of a second group of levels that are respectively less than the corresponding levels of the first group.

4. An automatic gain control circuit for maintaining the peak-to-peak amplitude of a signal having peaks that may extend on either side of a reference potential within predetermined limits comprising a signal channel including a gain changing means, said gain changing means having an input and an output for passing information signals, a signal magnitude detector having an input coupled to the input of said gain changing means and having an output, a peak detector having an input coupled to the output of said signal magnitude detector and having an output at which a voltage equal to the amplitude of the largest peak appears, gain control means having an input coupled to the output of said peak detector and an output coupled to said gain changing means, said gain control means including means for decreasing the gain provided by said gain changing means by predetermined increments as said voltage at the output of said peak detector increases through predetermined levels, and reset means responsive to the output of said peak detector and to the signals at the output of said signal magnitude detector for reducing the output voltage of said peak detector to zero when the amplitude of the signals at the output of said signal magnitude detector falls below a given fraction of the voltage at the output of said peak detector for a given period of time.

* * * * *

UNITED STATES PATENT AND TRADEMARK OFFICE
CERTIFICATE OF CORRECTION

PATENT NO. : 4,153,049
DATED : May 8, 1979
INVENTOR(S) : Ronald D. Gatzke et al

It is certified that error appears in the above-identified patent and that said Letters Patent are hereby corrected as shown below:

| | | |
|---|---|---|
| Column 5 | line 3 | after "$v_7$" and before "$v_8$" insert -- and -- |
| Claim 3 | line 2 | after "means" (first occurrence) delete -- (decreases) -- |
| | line 6 | after "means" (first occurrence) delete -- (increases) -- |

Signed and Sealed this

Eighteenth Day of September 1979

[SEAL]

Attest:

Attesting Officer

LUTRELLE F. PARKER
*Acting Commissioner of Patents and Trademarks*